US00PP33821P2

(12) United States Plant Patent
Koot

(10) Patent No.: US PP33,821 P2
(45) Date of Patent: Jan. 4, 2022

(54) ***CHAMAESYCE* PLANT NAMED 'DOCHASTADUCLEWHI'**

(50) Latin Name: *Chamaesyce hyperidifolia*
Varietal Denomination: Dochastaduclewhi

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/238,924

(22) Filed: Apr. 23, 2021

(51) Int. Cl.
*A01H 5/02* (2018.01)
*A01H 6/38* (2018.01)

(52) U.S. Cl.
USPC ..... Plt./302
CPC ..... *A01H 6/38* (2018.05)

(58) Field of Classification Search
USPC ..... Plt./302
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Chamaesyce* plant named 'Dochastaduclewhi', characterized by its relatively compact, mounding to semi-trailing plant habit; moderately vigorous growth habit; freely branching habit; freely flowering habit; and inflorescences with multiple white-colored flower bracts.

1 Drawing Sheet

Botanical designation: *Chamaesyce hyperidifolia.*
Cultivar denomination: 'DOCHASTADUCLEWHI'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Aug. 19, 2020, application number 2020/1946. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Chamaesyce* plant, botanically known as *Chamaesyce hypericifolia* and hereinafter referred to by the name 'Dochastaduclewhi'.

The new *Chamaesyce* plant is a product of a planned breeding program conducted by the Inventor in Rheinberg, Germany. The objective of the program is to create and develop new freely branching *Chamaesyce* plants with mounding plant habit, early flowering and multiple white-colored flowers per inflorescence.

The new *Chamaesyce* plant originated from a cross-pollination by the Inventor in July, 2017 of a proprietary selection of *Chamaesyce hypericifolia* identified as code number EW-0030, not patented, as the female, or seed, parent with a proprietary selection of *Chamaesyce hypericifolia* identified as code number EW-0008, not patented, as the male, or pollen, parent. The new *Chamaesyce* plant was discovered and selected by the Inventor as a single flowering plant within the progeny of the stated cross-pollination in a controlled greenhouse environment in Rheinberg, Germany in May, 2020.

Asexual reproduction of the new *Chamaesyce* plant by terminal vegetative cuttings in a controlled greenhouse environment in Rheinberg, Germany since June, 2020 has shown that the unique features of this new *Chamaesyce* plant are stable and reproduced true to type in successive generations of asexual reproduction.

SUMMARY OF THE INVENTION

Plants of the new *Chamaesyce* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dochastaduclewhi'. These characteristics in combination distinguish 'Dochastaduclewhi' as a new and distinct *Chamaesyce* plant:

1. Relatively compact, mounding to semi-trailing plant habit.
2. Moderately vigorous growth habit.
3. Freely branching habit.
4. Freely flowering habit.
5. Inflorescences with multiple white-colored flower bracts.

Plants of the new *Chamaesyce* differ primarily from plants of the female and male parent selection in growth habit as plants of the new *Chamaesyce* are more compact than and not as vigorous as plants of the parent selections.

Plants of the new *Chamaesyce* can be compared to plants of *Euphorbia hypericifolia* 'Inchadiacl', disclosed in U.S. Plant Pat. No. 32,682. In side-by-side comparisons, plants of the new *Chamaesyce* differ primarily from plants of 'Inchadiacl' in growth habit as plants of the new *Chamaesyce* are more compact than and not as vigorous as plants of 'Inchadiacl'. In addition, plants of the new *Chamaesyce* have narrower leaves and broader inflorescences than plants of 'Inchadiacl'.

BRIEF DESCRIPTION OF THE PHOTOGRAPH

The accompanying colored photograph illustrates the overall appearance of the new *Chamaesyce* plant showing the colors as true as it is reasonably possible to obtain in colored reproductions of this type. Colors in the photograph may differ slightly from the color values cited in the detailed botanical description which accurately describe the colors of the new *Chamaesyce* plant.

The photograph is a side perspective view of a typical flowering plant of 'Dochastaduclewhi' grown in a container.

DETAILED BOTANICAL DESCRIPTION

The aforementioned photograph and following observations and measurements describe plants grown during the spring and early summer in 22-cm containers in a glass-covered greenhouse in Rheinberg, Germany and under cultural practices typical of commercial *Chamaesyce* production. During the production of the plants, day and night temperatures averaged 18° C. and light levels averaged 4,500 lux. Plants were twelve weeks old when the photograph was taken and 25 weeks old when the description was taken. In the following description, color references are made to The Royal Horticultural Society Colour Chart, Fifth Edition, 2007, except where general terms of ordinary dictionary significance are used.

Botanical classification: *Chamaesyce hypericifolia* 'Dochastaduclewhi'.

Parentage:

- *Female, or seed, parent*.—Proprietary selection of *Chamaesyce hypericifolia* identified as code number EW-0030, not patented.
- *Male, or pollen, parent*.—Proprietary selection of *Chamaesyce hypericifolia* identified as code number EW-0008, not patented.

Propagation:

- *Type*.—Terminal vegetative cuttings.
- *Time to initiate roots, summer*.—About five days at temperatures about 20° C.
- *Time to initiate roots, winter*.—About seven days at temperatures about 20° C.
- *Time to produce a rooted young plant, summer*.—About three weeks at temperatures about 20° C.
- *Time to produce a rooted young plant, winter*.—About four weeks at temperatures about 20° C.
- *Root description*.—Fine, fibrous; typically white in color, actual color of the roots is dependent on substrate composition, water quality, fertilizer type and formulation, substrate temperature and physiological age of roots.
- *Rooting habit*.—Freely branching; medium density.

Plant description:

- *Plant and growth habit*.—Relatively compact, mounding to semi-trailing; inflorescences positioned above and beyond the foliar plane; moderately vigorous growth habit and moderate growth rate.
- *Branching habit*.—Freely branching habit; about three to five primary lateral branches each with numerous secondary lateral branches develop per plant.
- *Plant height*.—About 32 cm.
- *Plant diameter or spread*.—About 46 cm.
- *Lateral branch description*.—Length: About 26 cm. Diameter: About 5 mm. Internode length: About 5.6 cm. Aspect: Initially upright to outwardly to eventually semi-trailing. Strength: Moderately strong. Texture: Smooth, glabrous. Color: Close to 137C.
- *Leaf description*.—Arrangement: Opposite, simple. Length: About 2.9 cm. Width: About 8.5 mm. Shape: Elliptical. Apex: Acute. Base: Attenuate. Margin: Entire, not lobed. Venation pattern: Pinnate. Texture, upper surface: Pubescent; not rugose. Texture, lower surface: Pubescent; rugose. Color: Developing leaves, upper surface: Close to 144A. Developing leaves, lower surface: Close to 144B. Fully developed leaves, upper surface: Close to 137A; venation, close to 144B. Fully developed leaves, lower surface: Close to 138A; venation, close to 137A. Petioles: Length: About 1.1 cm. Diameter: About 0.7 mm. Strength: Moderately strong. Texture, upper and lower surfaces: Smooth, glabrous. Color, upper and lower surfaces: Close to 144B.

Inflorescence description:

- *Inflorescence type and habit*.—Inflorescences are composed of a single cyathia surrounded with about ten flower bracts subtending the cyathia; inflorescences positioned above and beyond the foliar plane; freely flowering habit with numerous inflorescences developing per plant; inflorescences face mostly upright to outwardly.
- *Inflorescence diameter*.—About 6.8 cm.
- *Inflorescence height*.—About 5.6 cm.
- *Fragrance*.—None detected.
- *Natural flowering season*.—Plants typically flower from the spring through the summer in northern Europe.
- *Inflorescence longevity*.—Inflorescences last about ten days on the plant; inflorescences persistent.
- *Flower bracts*.—Quantity per inflorescence: About ten. Length, largest bracts: About 1.1 cm. Width, largest bracts: About 2.6 mm. Shape: Elliptical to lanceolate; flat. Apex: Rounded to acute. Base: Attenuate, fused. Margin: Entire, not undulate. Texture, upper and surfaces: Smooth, glabrous. Aspect: Mostly horizontal. Venation pattern: Pinnate. Color: Developing bracts, upper and lower surfaces: Close to 155B. Fully developed bracts, upper and lower surfaces: Close to NN155D; venation, close to NN155D; color does not change with development. Flower bract petioles: Length: About 1.9 mm. Diameter: About 0.4 mm. Texture, upper and lower surfaces: Smooth, glabrous. Color, upper and lower surfaces: Close to 144B.
- *Cyathia*.—Quantity per corymb: One. Diameter: About 1.4 mm. Height: About 3 mm. Shape: Oval; sessile. Color: When developing and fully developed cyathia, upper surface: Close to 144B. When developing and fully developed cyathia, lower surface: Close to 144A. Nectaries: Quantity per cyathium: One. Length: About 0.5 mm. Width: About 0.5 mm. Shape: Oval. Texture: Smooth, glabrous. Color: When developing and fully developed nectaries, inner surface: Close to 144C and 155C. When developing and fully developed nectaries, outer surface: Close to 144C and 155C.

*Peduncles*.—Length: About 4.4 mm. Diameter: About 1.2 mm. Strength: Strong. Aspect: Incurved. Texture: Smooth, glabrous. Color: Close to 144A.

*Reproductive organs*.—Stamens: Quantity per cyathium: About six. Filament length: About 1.3 mm. Filament color: Close to 155C. Anther shape: Oval. Anther length: About 0.5 mm. Anther color: Close to 158C. Amount of pollen: Scarce. Pollen color: Close to 158D. Pistils: Quantity per cyathia: One. Pistil length: About 1.2 mm. Stigma shape: Crested. Stigma color: Close to 155D. Style length: About 0.5 mm. Style color: Close to 145C. Ovary color: Close to 144B.

*Seeds and fruits*.—To date, seed and fruit production has not been observed on plants of the new *Chamaesyce*.

Garden performance: Plants of the new *Chamaesyce* have been observed to have good garden performance and to tolerate wind, rain, temperatures ranging from about 8° C. to about 30° C.

Pathogen & pest resistance: Plants of the new *Chamaesyce* have not been shown to be resistant to pathogens and pests common to *Chamaesyce* plants.

It is claimed:

1. Anew and distinct *Chamaesyce* plant named 'Dochastaduclewhi' as illustrated and described.

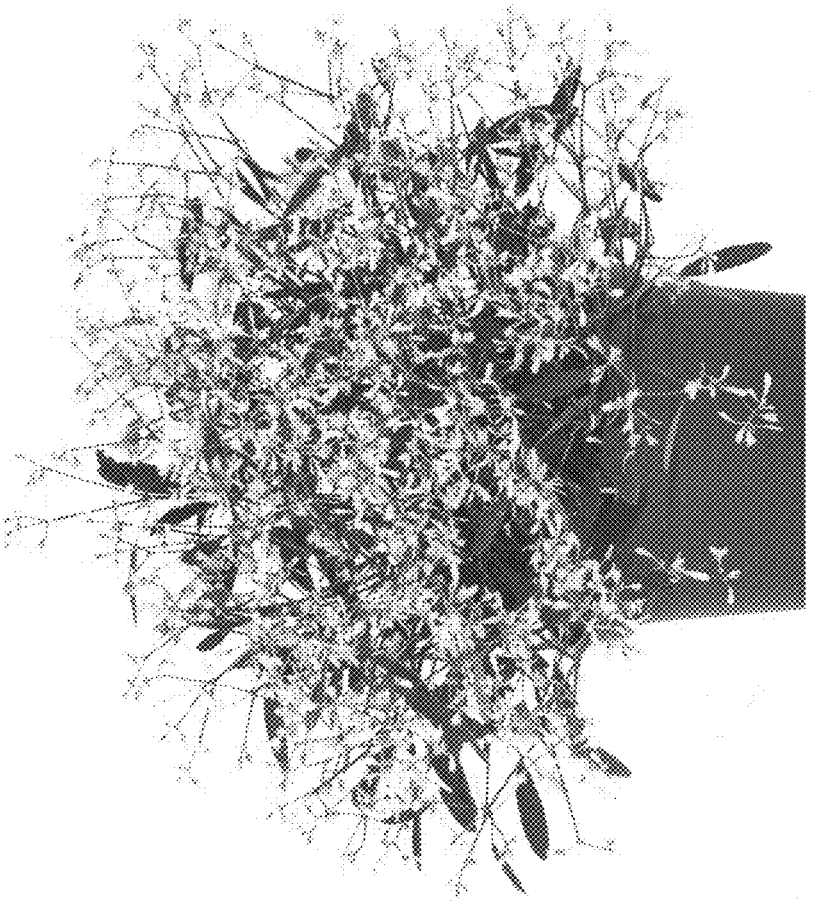

* * * * *